(12) United States Patent
Jakobsen et al.

(10) Patent No.: US 10,376,247 B2
(45) Date of Patent: Aug. 13, 2019

(54) CONTAINER ASSEMBLY AND ASSOCIATED METHOD

(71) Applicant: Biopsafe ApS, Vedbaek (DK)

(72) Inventors: Ole Jakobsen, Hellerup (DK); Christoffer Bay, Praesto (DK); Jacob Ilskov, Valby (DK)

(73) Assignee: Biopsafe ApS (DK)

( * ) Notice: Subject to any disclaimer, the term of this patent is extended or adjusted under 35 U.S.C. 154(b) by 0 days.

(21) Appl. No.: 15/584,545

(22) Filed: May 2, 2017

(65) Prior Publication Data

US 2017/0231604 A1    Aug. 17, 2017

Related U.S. Application Data

(63) Continuation of application No. 14/125,477, filed as application No. PCT/DK2011/050434 on Nov. 11, 2011, now Pat. No. 9,726,585.

(30) Foreign Application Priority Data

Jun. 14, 2011    (DK) .................................. 2011 70297

(51) Int. Cl.
| | | |
|---|---|---|
| *G01N 1/38* | (2006.01) | |
| *A61B 10/00* | (2006.01) | |
| *B65D 51/28* | (2006.01) | |
| *B01L 3/00* | (2006.01) | |
| *G01N 1/28* | (2006.01) | |

(Continued)

(52) U.S. Cl.
CPC .......... *A61B 10/0096* (2013.01); *B01L 3/502* (2013.01); *B65D 51/2835* (2013.01); *G01N 1/28* (2013.01); *G01N 1/38* (2013.01); *B01L 3/50853* (2013.01); *B01L 2300/047* (2013.01); *B01L 2300/0672* (2013.01);

(Continued)

(58) Field of Classification Search
CPC ....................................................... G01N 1/00
See application file for complete search history.

(56) References Cited

U.S. PATENT DOCUMENTS

| | | | |
|---|---|---|---|
| 3,521,745 A | | 7/1970 | Schwartzman |
| 4,247,001 A | * | 1/1981 | Wiegner ............ B65D 81/3222 206/222 |

(Continued)

FOREIGN PATENT DOCUMENTS

| | | |
|---|---|---|
| CL | 199802887 | 7/1999 |
| CL | 200102841 | 10/2002 |

(Continued)

OTHER PUBLICATIONS

Search Report for PCT/2013/003388, Completed by the INAPI Chile Patent Office, dated Nov. 25, 2013, 6 Pages.

(Continued)

*Primary Examiner* — Jyoti Nagpaul
(74) *Attorney, Agent, or Firm* — Brooks Kushman P.C.

(57) ABSTRACT

A tissue-sample container assembly including a container defining a cavity configured to store a tissue sample and a lid connectable to the container to close the cavity. The lid has a receptacle adapted to contain a preserving agent, a seal forming at least a portion of a bottom of the receptacle, and a puncturing member arranged above the seal and actuatable to break the seal. A preserving agent is disposed in the receptacle.

20 Claims, 13 Drawing Sheets

(51) Int. Cl.
  *B65D 43/02* (2006.01)
  *B65D 51/20* (2006.01)
(52) U.S. Cl.
  CPC ............. *B01L 2300/0832* (2013.01); *B01L 2400/0683* (2013.01); *B65D 43/0202* (2013.01); *B65D 51/20* (2013.01)

(56) References Cited

U.S. PATENT DOCUMENTS

| | | | |
|---|---|---|---|
| 4,353,868 | A | 10/1982 | Joslin et al. |
| 4,793,475 | A * | 12/1988 | Itzel .................. B65D 51/2814 206/219 |
| 4,889,992 | A | 12/1989 | Hoberman |
| 4,982,875 | A * | 1/1991 | Pozzi .................. B65D 51/285 222/129 |
| 5,145,646 | A * | 9/1992 | Tyranski ............ B01L 3/50825 215/235 |
| 5,152,965 | A | 10/1992 | Fisk et al. |
| 5,255,812 | A | 10/1993 | Hsu |
| 5,297,696 | A * | 3/1994 | Bernstein .................. B67B 7/26 222/83 |
| 6,197,260 | B1 | 3/2001 | Bradshaw et al. |
| 7,544,953 | B2 | 6/2009 | Goodman |
| 8,067,172 | B2 | 11/2011 | Stordeur et al. |
| 8,387,811 | B2 | 3/2013 | Livingston et al. |
| 8,485,987 | B2 | 7/2013 | Videbaek et al. |
| 2003/0222102 | A1 | 12/2003 | Cho |
| 2004/0013575 | A1 | 1/2004 | Stevens et al. |
| 2004/0228208 | A1 | 11/2004 | Papania et al. |
| 2007/0215496 | A1 | 9/2007 | Scarborough |
| 2009/0100944 | A1 | 4/2009 | Newby |
| 2009/0104692 | A1 | 4/2009 | Bartfeld et al. |
| 2009/0155838 | A1 | 6/2009 | Hale |
| 2010/0101340 | A1 | 4/2010 | Lipscombe |
| 2010/0140209 | A1 | 6/2010 | Valentine |

FOREIGN PATENT DOCUMENTS

| | | |
|---|---|---|
| CL | 2005002786 | 6/2006 |
| CL | 201001122 | 3/2011 |
| CN | 1969184 | 5/2007 |
| CN | 101472526 | 7/2009 |
| CN | 101835428 | 9/2010 |
| EP | 2647732 | 10/2013 |
| EP | 2647723 | 2/2017 |
| JP | H10260118 | 9/1998 |
| JP | H11242036 | 9/1999 |
| JP | 2007506403 | 3/2007 |
| JP | 2010511144 | 4/2010 |
| JP | 2011502254 | 1/2011 |
| JP | 2011505011 | 2/2011 |
| JP | 4689998 | 6/2011 |
| KR | 20050103807 | 11/2005 |
| KR | 20060082504 | 7/2006 |
| WO | 03031064 | 4/2003 |
| WO | 2004000678 | 12/2004 |
| WO | 2005005044 | 1/2005 |
| WO | 2007068094 | 6/2007 |
| WO | 2007137219 | 11/2007 |
| WO | 2007137272 | 11/2007 |
| WO | 2008040812 | 4/2008 |
| WO | 2009055311 | 4/2009 |
| WO | 2009055605 | 4/2009 |
| WO | 2009073152 | 6/2009 |
| WO | 2010020043 | 2/2010 |
| WO | 2011133854 | 10/2011 |

OTHER PUBLICATIONS

Danish Search Report for Application No. PA 2011 70297, Completed by the Danish Patent and Trademark Office dated Jan. 10, 2012, 1 Page.

Russian Office Action for Application No. 2013156531/15(08861), Completed by the Russian Patent Office, dated Oct. 27, 2015, 3 Pages.

English Summary for Japanese Office Action for Japanese Application No. JP 2014-515065, dated Jun. 23, 2015, 3 Pages.

International Search Report for PCT/DK2011/050434, Completed by the European Patent Office dated Jan. 23, 2012, 3 Pages.

* cited by examiner

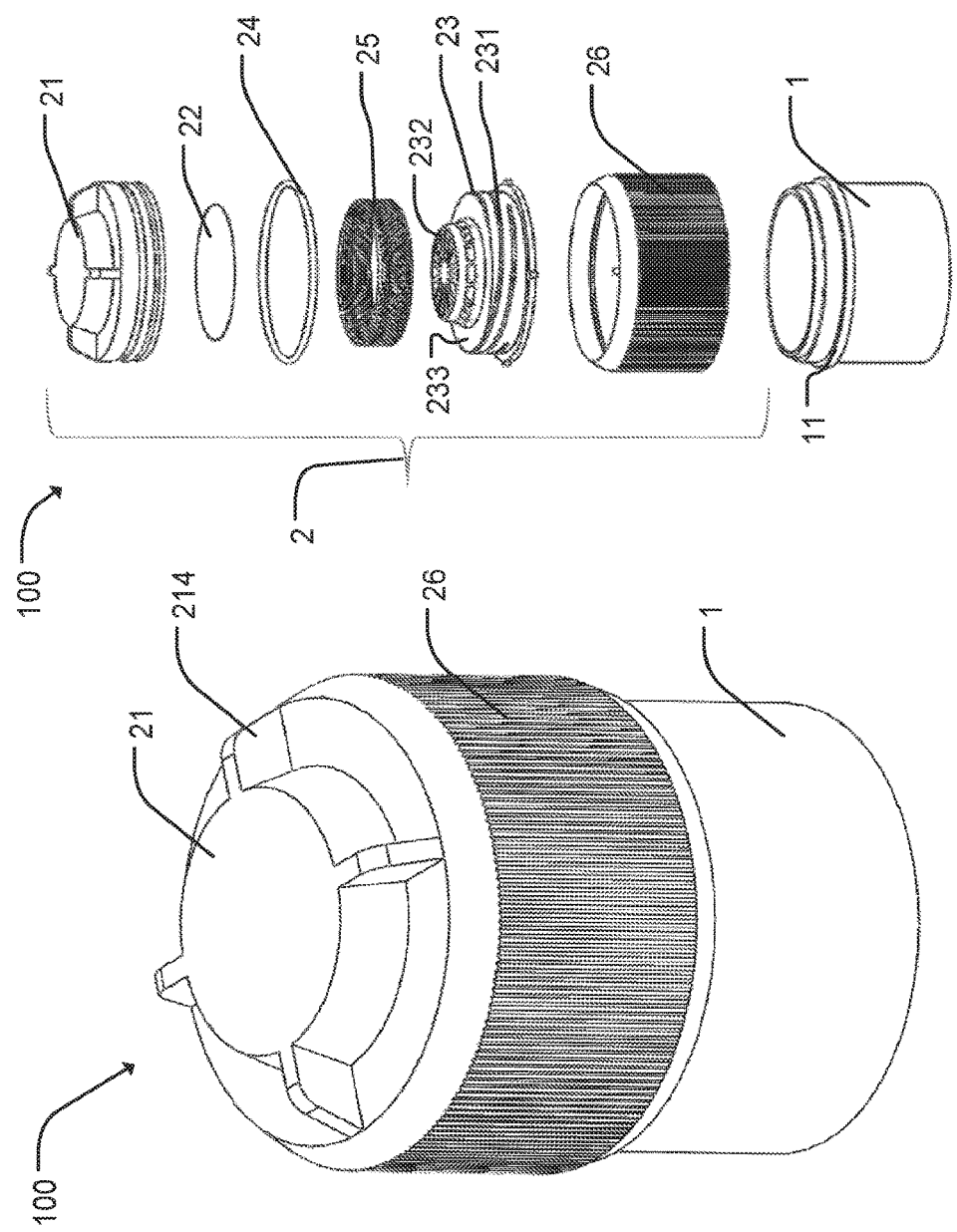

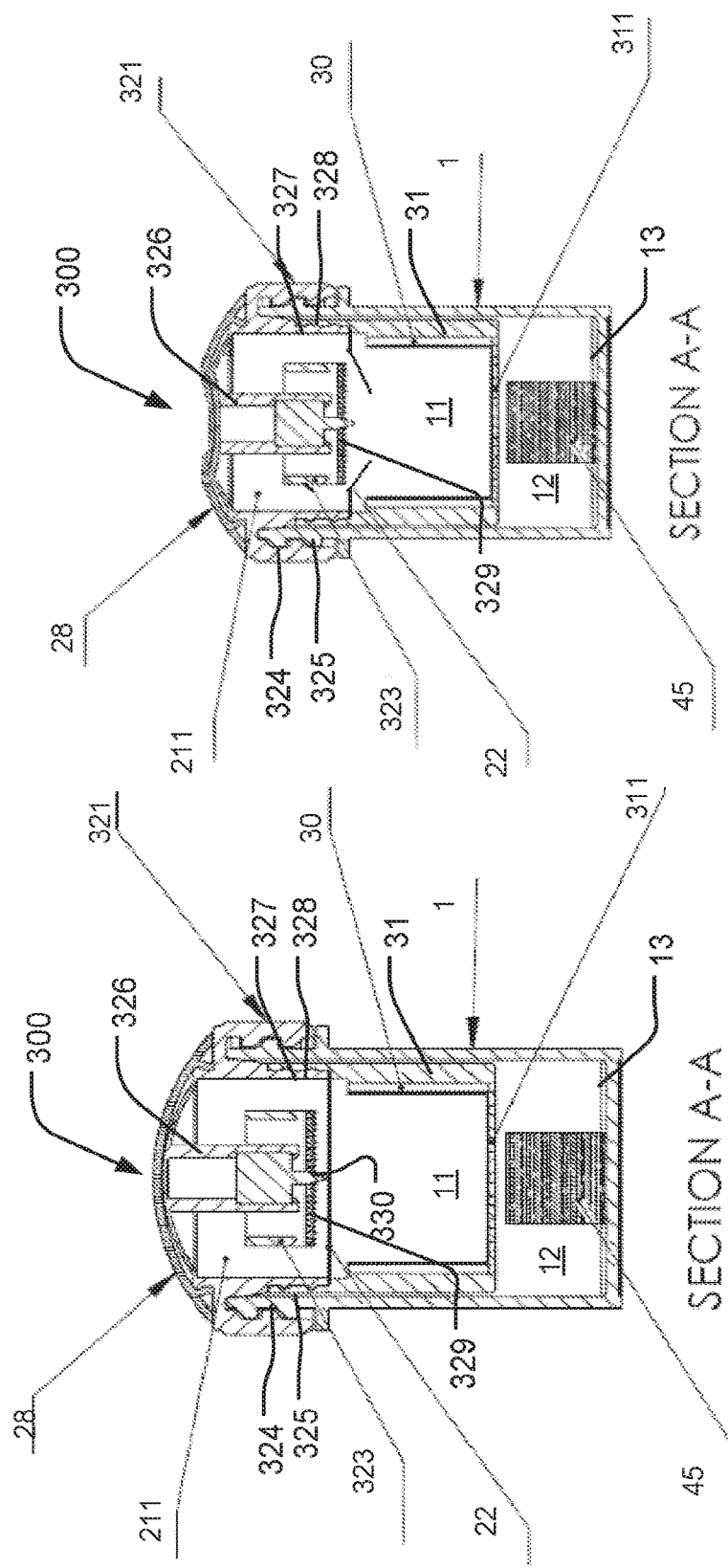

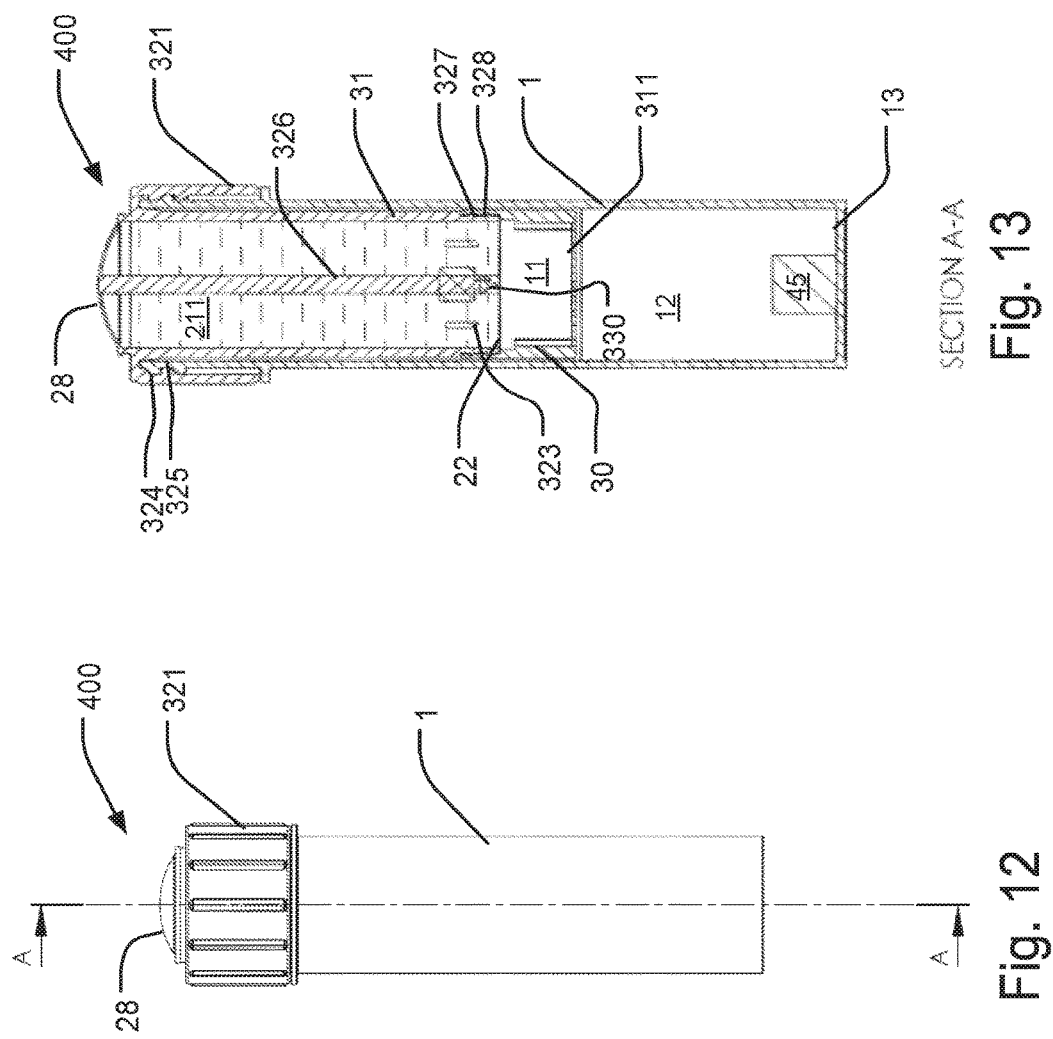

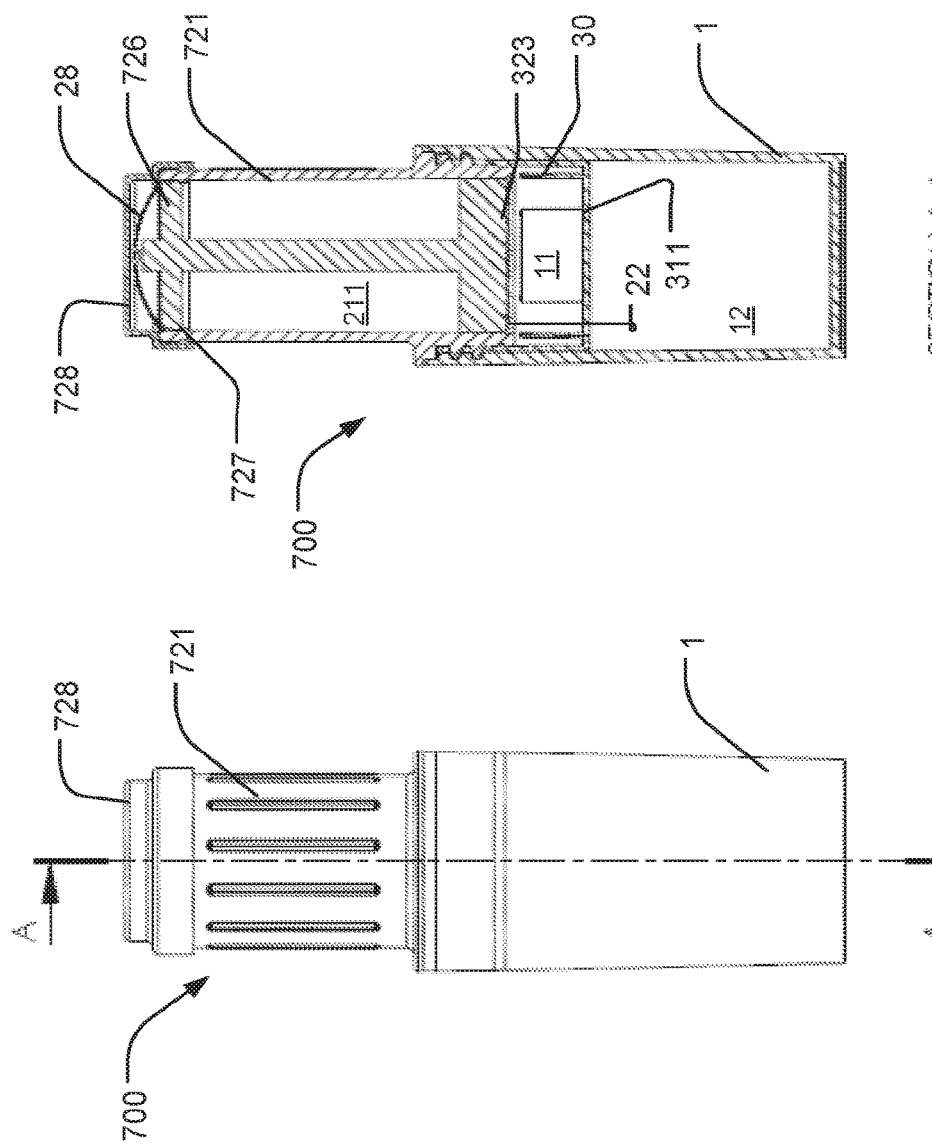

CONTAINER ASSEMBLY AND ASSOCIATED METHOD

CROSS-REFERENCE TO RELATED APPLICATIONS

This application is a continuation of U.S. application Ser. No. 14/125,477 filed Feb. 8, 2014, now U.S. Pat. No. 9,726,585, issued Aug. 8, 2017, which is the U.S. National Phase of PCT Application No. PCT/DK2011/050434 filed on Nov. 11, 2011, which claims priority to DK Patent Application No. PA 2011 70297, filed on Jun. 14, 2011, the disclosures of which are incorporated in their entirety by reference herein.

TECHNICAL FIELD

The present disclosure relates to a container assembly for storing a tissue sample and to a method of preserving a tissue sample.

BACKGROUND

Container assemblies for releasing an agent into a container at a desired point in time are well known and come in many shapes and sizes, both within the industry as well as within consumer goods.

In hospitals and clinics containers or Petri dishes are used for collecting and storing tissue samples, such that after a tissue sample has been taken from a patient, the tissue sample is placed in a container, and a preserving agent, often formalin, is subsequently filled in the container before the container is closed and sent off to a laboratory for analysis. Here the container is usually opened in a fume cupboard as formalin and other preserving agents are toxic to inhale. The problem with this is that in the hospital the personnel taking the tissue sample, have to handle a preserving agent on a daily basis when filling the container. Usually a formalin dispenser station or a dispenser mountable on the container temporarily is used. After the formalin has been dispensed into the container, the lid is mounted on the container. Handling of a preserving agent this way may result in spillage and inhalation. Inhalation and other exposures constitute is a health hazard and handling of formalin and other preserving agents should be carried out with great care.

WO2004/000678 describes different embodiments of mixing vials, in particular the embodiment depicted in FIGS. 6A-B show a mixing vial where a rigid rod is pressed through a supplemental container and the dilutant is entered into the container.

U.S. Pat. No. 5,152,965 describes an assembly of containers, comprising a reagent vial and a container adapted to engage with an adapter assembly positioned between the two. The reagent vial contains a reagent to be mixed with a reagent diluent in the container. The adapter assembly comprises a coupler and a hollow plunger. The reagent vial is engageable with the coupler in a first position and is advanceable into a second position relative to the adapter assembly such that the hollow plunger thereof displaces the seal of the reagent vial permitting the reagent to flow through the hollow plunger to mix with diluent in the container.

The advancement of the coupler results in an increased pressure in the container, which is undesirable as the increased pressure might result in a spillage of the content in the container, when the adapter assembly is removed from the container.

WO2008/040812 describes a receptacle configured to receive a volume of preserving agent, and a lid containing the preserving agent and being adapted to be coupled to a tissue storage container. The preserving agent is entered into the lid through a one way valve. The lid further comprises a membrane with a number of holes. A plastic disc containing an equal amount of holes is placed between the receptacle and the membrane in the lid. When the holes are brought into alignment, e.g. by twisting the lid, the preserving agent flows into the receptacle. This requires that the container assembly is oriented such that the cover facing upwards, thereby allowing the preserving agent to flow into the container assisted by gravity.

SUMMARY

The object of the present invention is to provide a container assembly where the risk of spillage and evaporation is considerably reduced and risk of the sample getting stuck to the cover is eliminated.

In a first aspect, this is achieved by providing a container assembly comprising a separator positioned between the seal and the bottom of the container, and the separator is provided with at least one aperture adapted to provide a fluid passage between the receptacle and the container.

By positioning the separator between the receptacle and the bottom of the container, it is ensured that the tissue sample does not get stuck to the top member or the puncturing means and at the same time that the seal does not interfere with the tissue sample. The tissue sample will usually be positioned at the bottom of the container.

According to a preferred embodiment the container assembly further comprising a space between the separator and the seal, the separator being provided with a conduit adapted to provide a fluid passage between the space and the container. This enables air from the container to travel upwards and thereby making it easier for the preserving agent to enter the container through the separator.

The conduit may have an opening positioned above the level of the preserving agent after the seal has been broken. Thereby the air in the container below the separator bypasses the preserving agent, making it easier for the preserving agent to enter the container below the separator.

The cover may constitute a lid. Instead of having to remove the cover after having released the content in the receptacle, the cover may stay on the container and function as a lid, making it easy to transport.

The cover may comprise a membrane having a substantially convex shape in the first position and a substantially concave shape in the second position. This membrane preferably covers the puncturing member. The different shapes of the membrane in the first and second position, makes it possible for the personnel to see from above if the seal has been broken.

The cover is preferably adapted to be fluid tightly sealed to the container. This contributes to reducing the risk of spillage.

The cover may comprise a protective cap for covering the membrane. Thereby it is ensured that the membrane and thereby the puncturing member is not pressed accidentally and the seal is not broken when it is not intended to.

The container assembly may comprise a tracking device, such that the tissue sample can be tracked from where it was taken all the way to the laboratory. The container assembly may also comprise a temperature tracker, such that it is possible to see if the tissue has been subjected to heat or cold, which may affect the tissue sample and consequently the results of a test.

The puncturing member may be provided with at least one aperture, for providing a passage between the space and the container. This eases the flow of the preserving agent into the container. The preserving agent may flow around the puncturing member as well.

The separator may comprise a bottom and, engagement means for engagement with corresponding engagement means of the cover, such that the bottom of the separator is prevented from contacting the bottom of the container. The tissue sample does therefore not risk being pressed or squashed when in the container and when the cover is removed for entering or taking out the tissue sample, the separator stays connected to the cover and does not get in the way when handling the tissue sample. The engagement means may for example be threads or a snap closure.

An outer diameter of the separator may be substantially equal to an inner diameter of the container, such that the separator and the container substantially fit together and little fluid may bypass the separator.

The seal may be selected from a group consisting of a film, a foil, a membrane and a polymer. These are all materials that are suitable to be either punctured or cut or in any way penetrated, such that the preserving agent may escape.

A part of the container assembly may comprise a transparent part for viewing inside the container. This enables the user of the container assembly to visually inspect the sample to see if a proper preservation has been carried out or whether the preserving agent has been released from the receptacle into the container.

The assembly may be provided with an indicator for indicating whether the seal has been broken. This can be seen as an indicator of whether the content of the receptacle has been compromised, if the seal has been damaged contaminants might enter the receptacle, or whether the content of the receptacle has been released and thereby alert the user. If the content has been released, the user knows that the container should not be opened without taking different safety measures, such as opening the container in a fume cupboard.

The separator is preferably a contrast colour, such as blue, to a colour of the tissue. This makes it easier the see the tissue sample if it gets stuck to the separator during transport e.g. to the laboratory.

The puncturing member may be provided with at least two projections for breaking the seal, such that more holes are created it the seal and the preserving agent may more easily leave the receptacle and enter the container.

By providing the puncturing member with teeth, the seal may be broken or pierced in several places easing the flow of preserving agent into the container.

The cover may be adapted to be locked to the container. This secures that there cannot be any tampering with the tissue samples.

According to another embodiment the container assembly may comprise a container for storing a tissue sample, a cover adapted to engage with the container, wherein the cover comprises: a top member comprising a receptacle, wherein the receptacle is adapted to contain a preserving agent, a seal for sealing off said receptacle, a punching or puncturing member for breaking said seal wherein the seal is broken by displacing the punching or puncturing member, a volume where the volume is defined by the interior of the outer walls of the container assembly, wherein the punching or puncturing member is provided with engagement means adapted to engage with corresponding engagement means provided on the top member, such that the position of the punching or puncturing member is adjustable independently of the orientation of the container assembly, the container assembly has a first and a second position, wherein in the first position the container is separate from the receptacle, and in the second position fluid communication is provided between the receptacle and the container, wherein the volume in the first position is the same as the volume in the second position. By not changing the volume of the container assembly, the pressure inside the container remains the same and thereby the risk of spillage when opened is considerably reduced.

The punching or puncturing member may be adapted to support the seal after the seal has been broken. By letting the punching or puncturing member support the seal the risk of parts of the seal slipping into the container after the seal has been broken, and mixing with the content here, is reduced.

The cover may further comprise a ring member adapted to engage with said container. This ensures that the cover is connectable to the container.

The seal may be broken from outside of the receptacle. By not having to mount any punching or puncturing means within the receptacle, the risk of spillage during mounting of the cover is reduced and the risk of any contaminants getting into the receptacle is reduced, and the shelf life of the assembly is increased.

The punching or puncturing member and the receptacle may be adapted to substantially fit together. This means that they are shaped such that they leave minimum room for anything being positioned between the two, except for the broken seal, when the punching or puncturing member has been displaced to its terminal position. The terminal position is defined as a position where the punching or puncturing member cannot be displaced further from its initial position. This reduces the risk of any preserving agent flowing from the container back into the receptacle behind the punching or puncturing member, thereby separating the tissue sample from the preserving agent.

At least a part of the space in the receptacle may form part of the space in the container, when the cover is mounted on the container and the seal has been broken. This means that the punching or puncturing member is displaced such that when the seal has been broken, the punching or puncturing member functions as a new separator between the receptacle and the container and at least some of the space in the receptacle now forms part of the container where the tissue sample may be present.

The punching or puncturing member may only be able to advance when the cover is mounted on the container. This secures that the seal is not accidentally broken, and the preserving agent may leak.

The punching or puncturing member may only be able to advance when the top member is pushed down simultaneously with being turned. This secures that even when the top member is mounted on the container, the seal is not accidentally broken.

The cover may comprise resilient means for urging the punching or puncturing member away from the receptacle. This enables the opening of the cover by simultaneously pushing and turning of the cover. Additionally it contributes to ensuring that the seal does not rest on the punching or puncturing member and thereby increasing the risk of unintentionally breaking the seal.

The receptacle may comprise an opening and a bottom, wherein the receptacle may be tapered towards the bottom.

By making the receptacle tapered, a faster release of the preserving agent is obtained and it is not possible for any of the preserving agent to not be released into the container when the seal is broken. The receptacle may also be straight or cylindrical.

According to a second aspect a method of preserving a tissue sample, comprises the steps of: providing a container, filled with a preserving agent and sealed off by a seal, a puncturing member and a separator, placing a tissue sample in said container, engaging said cover with the container thereby positioning said separator between the seal and the bottom of the container, displacing the puncturing member whereby said seal is broken and the preserving agent is allowed to enter into the container through the separator.

The puncturing member is preferably displaced by pressure on the puncturing member.

A different method of providing a container assembly for containing a tissue sample may be provided, comprising the steps of: providing a container, providing a cover including a top member with a receptacle and punching or puncturing member, filling said receptacle with a preserving agent, sealing said receptacle with a seal, placing a tissue sample in said container, engaging said cover with the container, displacing the punching or puncturing member by engaging engagement means of the punching or puncturing member with engagement means on the top member of the cover, whereby the seal is broken and the preserving agent is entered into the container.

Any features from the first aspect may be incorporated into the second aspect, and vice versa.

BRIEF DESCRIPTION OF THE DRAWINGS

In the following, the invention will be described in further detail with reference to the drawings in which:

FIG. 1 shows a perspective view of the container assembly in a first embodiment, FIG. 2 shows an exploded view of the container assembly shown in FIG. 1, FIG. 9 shows a cross section of the container assembly in a first position in the third embodiment, FIG. 10 shows a cross section of the container assembly in a second position in the third embodiment, FIG. 12 shows a perspective view of the container assembly in a fourth embodiment, FIG. 13 shows a cross section of the container assembly in a first position in the fourth embodiment.

FIG. 20 shows the container assembly in an assembled state in a seventh embodiment.

FIG. 21 shows a cross section of the container assembly in a first position in a seventh embodiment.

DETAILED DESCRIPTION

Figure 3:
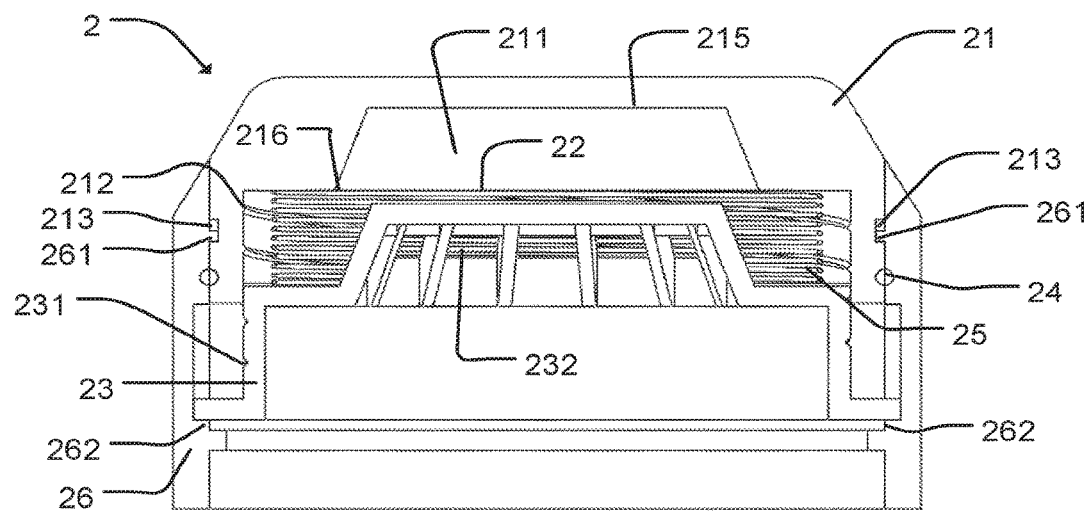
FIG. 3 shows a detailed view of a cross section of the cover in the first embodiment.

Like reference numbers refer to like features throughout the drawings.

FIG. 1 shows a container assembly generally designated 100 and comprising a container 1 for containing a tissue sample and a cover 2 in an assembled state. In the embodiment shown the cover 2 comprises a ring member 26, which is grooved for a firmer grip, and a top member 21. The ring member 26 may be provided with a rubber surface or simply with a smooth surface instead. The top member 21 is provided with projection(s) 214 for making it easier to get a hold on the top member 21, when the top member 21 is to be turned. The cover constitutes a lid, making the container assembly easy to transport. In the embodiment shown the container assembly is in an assembled state maximum 35 mm thick or deep or long on one of its sides, which makes it possible to send it in a letter. The container assembly may also be a maximum of 20 mm on one of its sides, 25 mm on one of its sides or 50 mm on one of its sides. The container assembly may be larger on one of its sides, or even smaller on one of it sides. The receptacle in this embodiment is adapted to contain 10 ml of preserving agent, such as formalin. The receptacle may be able to contain a different amount of preserving agent, such as less than 15 ml, less than 20 ml, less than 25 ml, less than 50 ml, less than 100 ml or less than 10 ml preserving agent or more than 100 ml of preserving agent. The container 1 is at least able to contain the corresponding amount of preserving agent as well as a tissue sample. A tissue sample may take up up to 1 cm$^3$, but is likely to be smaller, down to 1 mm$^3$. The tissue sample may be able to be covered by the preserving agent no matter the orientation of the assembly.

FIG. 2 shows the different parts of the container assembly 100 in a first embodiment. In addition to the top member 21, the cover comprises a seal 22 in the form of a foil. The seal may also be a film, a membrane, a polymer, a composite material or glass. The top member 21 is made of a polymer material, but may be made of other materials such as glass. In the embodiment shown the cover 2 further comprises a packing 24 in the form of an O-ring for sealing the connection between the ring member 26 and the top member 21. Other sealing means may be used.

Between a punching or puncturing member 23 and the top member 21 is resilient means 25 in the form of a spring positioned, for urging the punching or puncturing member 23 away from the seal 22. In other embodiments the resilient means 25 may be made of another resilient material such as rubber or it may be in the form of flexible rods positioned around the circumference of the punching or puncturing member 23 or inside the top member 21 along the circumference of the receptacle 211. The rods may be made of a polymer or a metal. The resilient means 25 may be integrated with either the top member 21 or the punching or puncturing member 23.

In this embodiment the punching or puncturing member 23 in the form of a punch or a plunger is provided with apertures 232 in an area of the punching or puncturing member 23 that is adapted to enter the receptacle 211. The apertures 232 contribute to facilitating a fluid communication between the receptacle and the container 1. The punching member or puncturing 23 may also, or alternatively, be provided with apertures along flange 233, which is not intended to enter the receptacle 211. The punching or puncturing member 23 is hollow but it may also be solid and provided with one larger aperture or several smaller apertures for facilitating a fluid communication between receptacle 211 and the container 1. By making the punching or puncturing member 23 solid and making it fit together in shape with the receptacle 211 or only providing the punching or puncturing member 23 with aperture(s) along the flange 233, the receptacle 211 is either almost filled by the punching or puncturing member 23 or the connection between the receptacle 21 and the container 1 is sealed off when the punching or puncturing member 23 has reached its terminal position. This prevents the preserving agent from becoming separated from the tissue sample. Only a minimal part or nothing of the preserving agent can flow back into the receptacle 211 and into a space that is not reachable to the tissue sample, because the tissue sample may be larger than the provided apertures.

Finally, the container assembly 100 comprises the container 1 adapted to engage with ring member 26. The engagement between the two can either be done via threads or via a press on cover, by pressing a resilient circumferential flange on the ring member 26 over a flange or other projections on the container 1 or vice versa. The ring member 26 is in this embodiment used for holding the container 1 and the top member 21 together and it contributes to controlling how far the top member 21 may be pushed down.

The container 1 and/or the cover 2 may be provided with a transparent part for viewing inside the container 1 to see if a tissue sample is in the container 1 or if the seal 22 has been broken and the preserving agent is in the container 1. The container 1 and the cover 2 may be provided with a locking mechanism to prevent tampering with the tissue sample on the way from the hospital to the laboratory. The locking mechanism may be of a kind that may only be opened by the laboratory personnel or it may be an indicator showing if the assembly 100 has been opened.

FIG. 3 shows a close up view of an embodiment of the cover 2 in an assembled state.

As shown in detail in this figure, the top member 21 is provided with the receptacle 211 inside the top member 21 in the embodiment shown. The top member 21 is further provided with engagement means in the form of indentations 213. These are adapted to engage with projections 261 provided on the ring member 26. The engagement between the two retains the top member 21 in position as well as provides a safety margin of how far down the top member 21 may be pushed. If such movement limiting means was not present it would be possible to accidentally press the top member 21 and break the seal 22. Additionally, the ring member 26 is provided with projection(s) 262 that keep(s) the punching or puncturing member 23 in place. In the embodiment shown the punching or puncturing member 23 is provided with threads 231 that are adapted to engage with threads 212 inside the top member 21. These make sure that the punching or puncturing member 23 cannot merely be pushed from below, such that the seal 22 breaks unintentionally. When it is desired to break the seal 22, the top member 21 is advanced such that the seal 22 breaks. In this embodiment the top member 21 must be turned at the same time the top member 21 is being pushed from above simultaneously with the punching or puncturing member 23 being pushed from below. The punching or puncturing member 23 is being pushed from below by the container 1. Before breaking the seal 22 the cover 2 and the container 1 is preferably fluid tightly coupled.

In the embodiment shown, the receptacle 211 is tapered such that the opening of the receptacle 516 is wider than the bottom 215. The receptacle may be other shapes such as cylindrical, pyramid shaped polygonal or other shapes. Correspondingly the punching or puncturing member may have the same shape.

In all of the embodiments the receptacle in the cover may be filled with a preserving agent at the site where the cover is being manufactured or at least before the cover is delivered to the user. The receptacle may be filled with a preserving agent through the opening, which is later sealed off by the seal.

Figure 4:
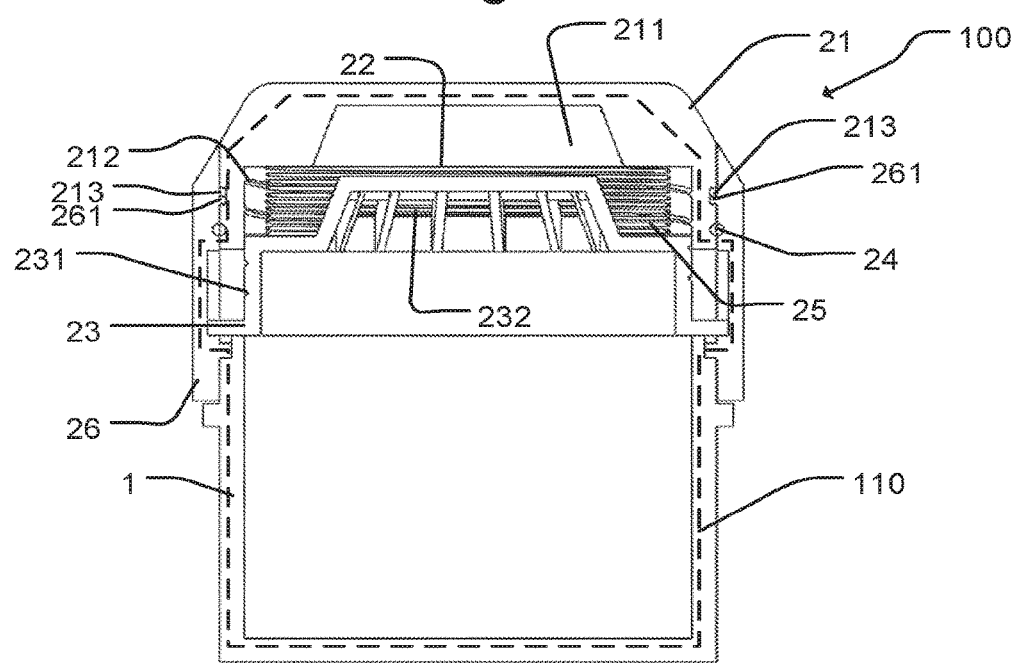
FIG. 4 shows a cross section of the container assembly in a first position in the first embodiment.

From the embodiment in FIG. 4 it can be seen how the punching or puncturing member 23 rests on the edge of the container 1 and by mounting the cover 2 on the container 1 the punching or puncturing member 23 is pushed slightly upwards. This makes sure that the punching or puncturing member 23 is only able to advance when the cover 2 is mounted on the container 1. The engagement means 231 and 212 is still not able to engage if the top member 23 were turned. In this embodiment the top member 21 must be pushed down as well. This added security that the top member 21 must be pushed down as well to break the seal 22 may be left out.

Instead of advancing the engagement of the engagement means on the top member 212 with the engagement means on the punching or puncturing member 231, by turning the top member 21, it may be possible to have a sudden release of the preserving agent, where the seal 22 is broken by pushing the top member 21 down without turning the top member 21. In this case the indentation 213 extends further upwards and does not stop the projection 261 until after the seal 22 has been broken.

Between the ring member 26 and the container 1 a further packing (not shown) may be provided for added sealing between the two.

The broken line encircles the volume 110 that does not change during breaking of the seal 22. The volume 110 is defined by the interior of the outer walls of the container assembly 100. This is the interior wall of the top member 21, the ring member 23 and the container 1. Where the parts overlap, it is the parts being the most interior that define the volume.

Figure 5:
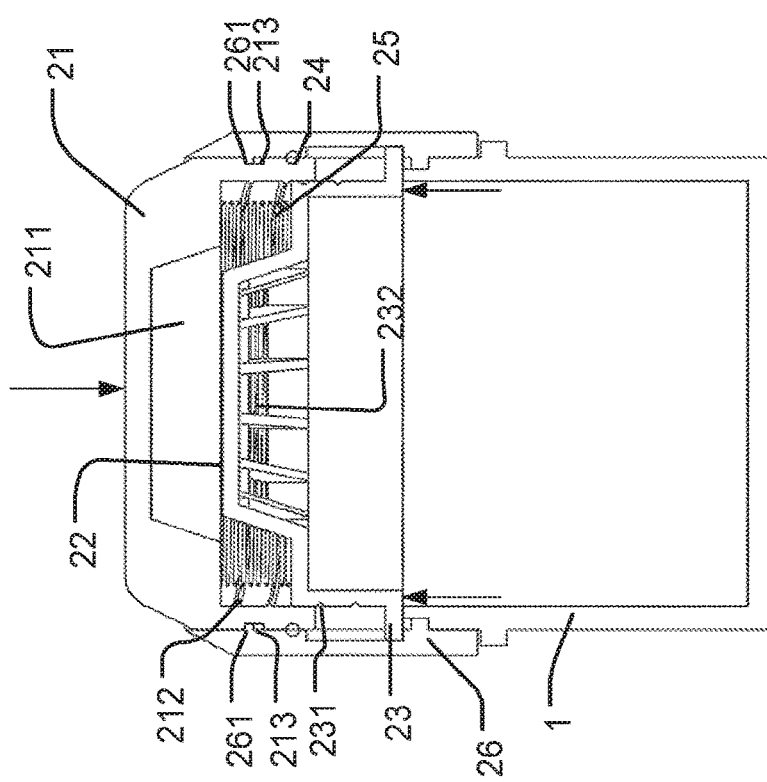
FIG. 5 shows a cross section of a first embodiment of the container assembly in a first position with the lid slightly pushed down.

In FIG. 5 the top member 21 has been pushed down as can be seen on the engagement between the projection 261 and the indentation 213. The punching or puncturing member 23 is ready to engage with the top member 21. By turning the top member 180-360 degrees the punching or puncturing member is forced through the seal and the seal is broken. The seal 22 is broken from below meaning that the punching or puncturing member 23 is outside the receptacle 211 before the seal 22 is broken. The top member may be turned more or less to break the seal 22 and to reach its terminal position.

Figure 6:
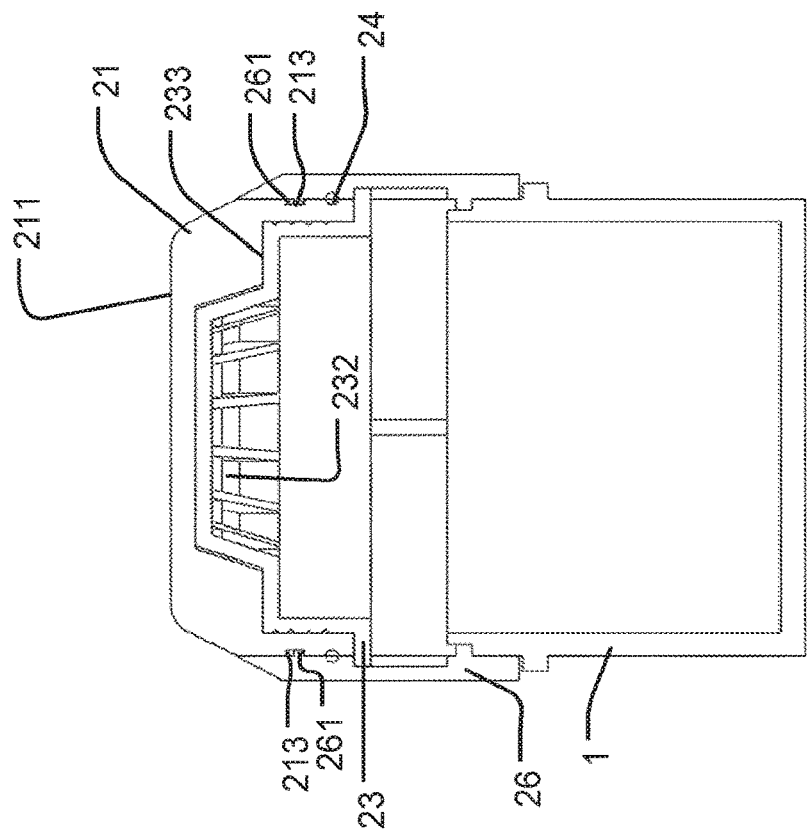
FIG. 6 shows a cross section of a first embodiment of the container assembly in a second position where the seal has been broken.

FIG. 6 shows the punching or puncturing member 23 in the terminal position. The top part of the punching or puncturing member 23 above the flange 233 fits exactly into the receptacle 211. The top part of the punching or puncturing member may be smaller or bigger than the receptacle 211. After the seal has been broken, it is positioned between the top member 21 and the punching or puncturing member 23, and the seal 22 is prevented from entering into the container 1. The punching or puncturing member 23 supports the seal 22 after the seal 22 has been broken. The seal 22 might also be of such a kind that upon puncturing the seal draws out to the sides, leaving nothing but a ring of sealing material along the edge of the opening of the receptacle 216. The space that is left when the punching or puncturing member 23 has reached its terminal position is preferably less than 1/20 of the space in the receptacle from opening 216 to bottom 215 or the distance from the bottom of the receptacle 215 to the punching or puncturing member 23 is less than 1 mm.

The FIGS. 1-6 show the different positions or states that the container assembly may have.

In FIGS. 1-3 a container, a cover is provided including a top member with a receptacle and punching or puncturing member. In FIG. 3 the receptacle is filled with a preserving agent and the receptacle is sealed. In FIG. 4 a tissue sample (not shown) is placed in the possibly empty container and the cover is brought into engagement with the container. In FIG. 5 the top member is pushed down and in FIG. 6 the punching or puncturing member is displaced by engaging engagement means of the punching or puncturing member with engagement means on the top member. The seal is consequently broken or punctured and the preserving agent is allowed to enter into the container.

Figure 7:
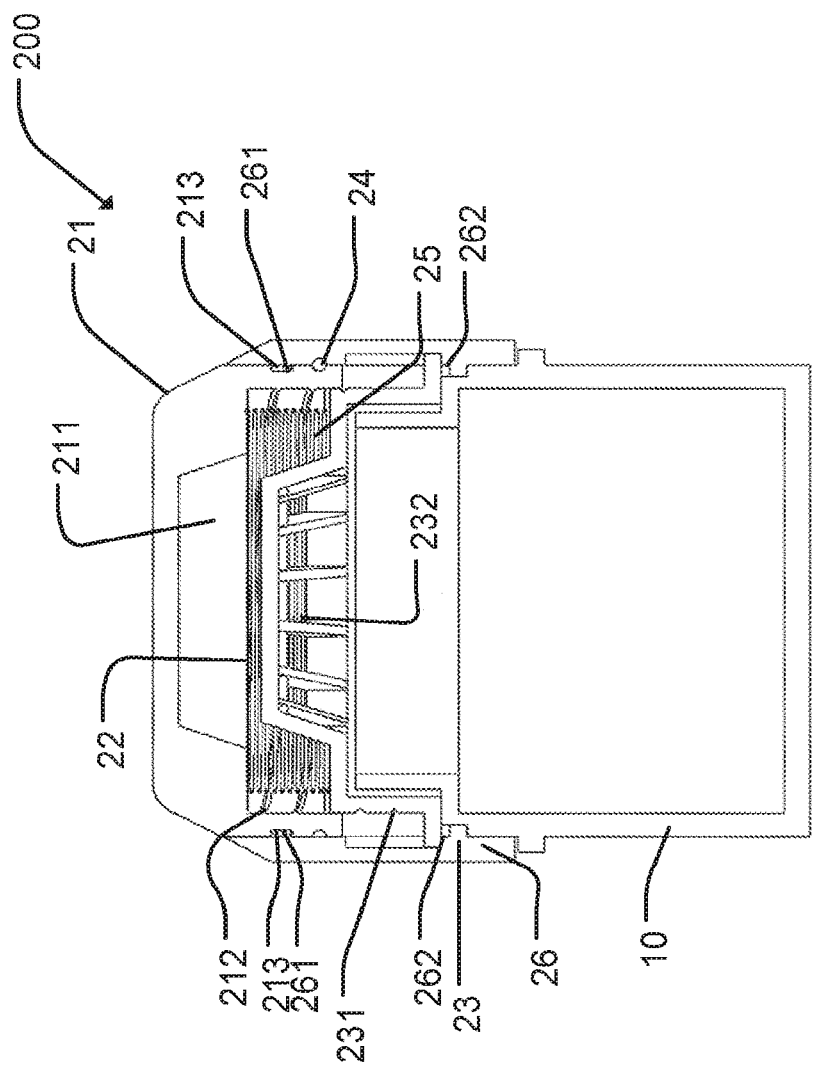
FIG. 7 shows a view corresponding to FIG. 3 of the container assembly in a second embodiment.

FIG. 7 shows a container assembly in a second embodiment. The second embodiment works as described for the first embodiment and the features with the same reference number are the same. The difference here is that the container 10 is extending up into the punching or puncturing member 23. The punching or puncturing member 23 thereby has the option to rest on the projection 262 on the container or on the edge of the container. So that it is either the projection 262 that pushes the punching or puncturing member 23 up, or it is the edge of the container. By making the container extend into the punching or puncturing member the personnel opening the container assembly is better protected from spillage as the wall above the level of preserving agent in the container is higher.

Figure 8:
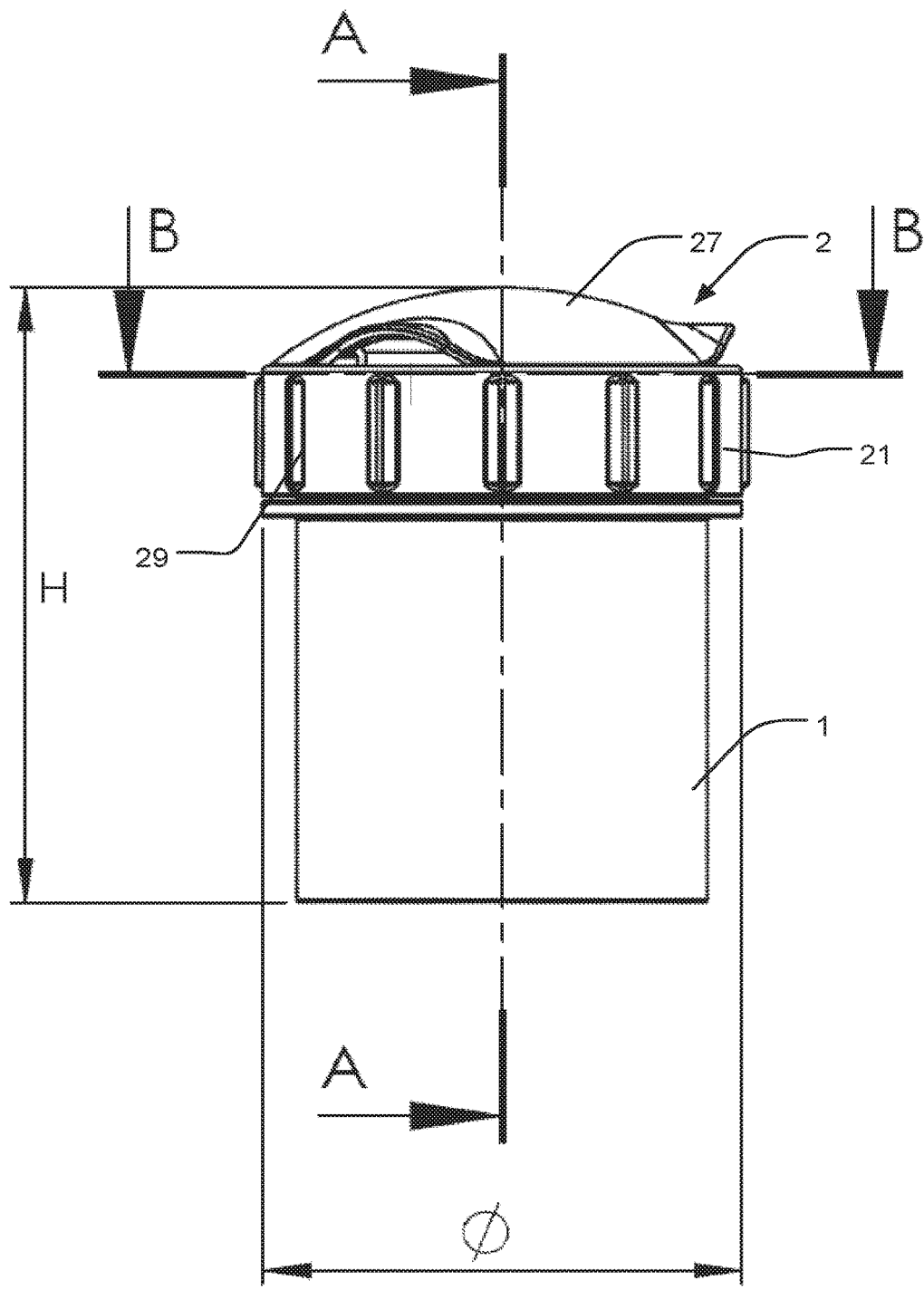
FIG. 8 shows a perspective view of the container assembly in a third embodiment.

FIGS. 8-11 shows a third embodiment of the invention. Referring to FIG. 8, the assembly comprises a container 1 and a cover 2, the cover 2 comprising a protective cap 27 and a top member 21. The purpose of the protective cap 27 is to secure that the membrane (see FIGS. 9 and 10) is not pressed unintentionally. The protective cap 27 may be pivotable or removable. The top member 21 is provided with projections 29 for an easy grip and is removed from the container 1 by turning. The diameter Ø of this embodiment is 33 mm, but may be smaller or bigger. The height H is 47 mm, but may be smaller or bigger. The receptacle 211 may be higher such that more preserving agent may be contained. The receptacle 211 and the container 1 should preferably be able to contain about 20 ml preserving agent, respectively.

Figure 11:
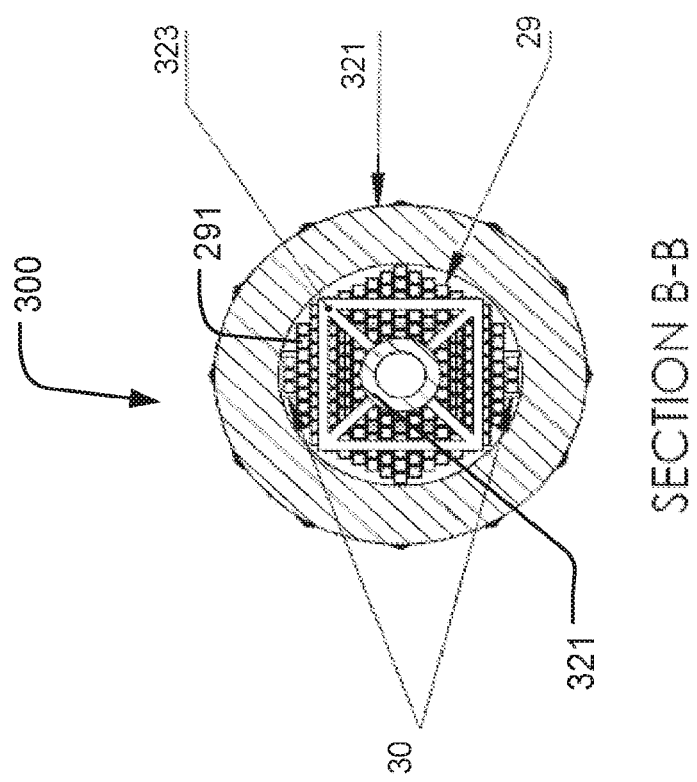
FIG. 11 shows a cross section of the container assembly in the third embodiment.

In FIG. 9 the assembly is in the first position and in FIG. 10 in the second position. The cross section in FIGS. 9-10 is taken along the line A-A as shown in FIG. 8, and FIG. 11 is a cross section along the line B-B also shown in FIG. 8. The container 1 is adapted to receive a tissue sample 45, and the cover comprises a top member 321. A separator 31 is provided between the seal 22 and the bottom 13 of the container. In this way, in a mounted state with the cover attached the container 1, the container 1 is separated into two spaces, a first 11 and a second 12 space. Even though the spaces 11, 12 are separated does not necessarily mean that the separator 31 and the container 1 are fluid tightly sealed. Fluid may be prevented from bypassing the separator 31. Fluid may also bypass the separator 31 instead of traveling though the separator 31. The inner circumference of the container 1 is of substantially same size as the outer circumference of the separator 31, but the inner circumference of the container 1 may be slightly bigger than the outer circumference of the separator 31.

Referring to FIGS. 9-10, the top member 321 is provided with engagements means 324, such as threads, for engagement with the container 1. The container 1 is likewise provided with engagement means 325, here in the form of threads for engagement with the corresponding threads on the top member 321. The engagement between the top member 321 and the container 1 may alternatively be accomplished by means of a snap closure. Furthermore, the top member 321 is provided with engagement means 326 for engagement with the puncturing member 323. The engagement means 326 is in the form of four slits in a hollow cylindrical shape that is adapted to receive the puncturing member 323. The cylindrical shape may be solid and/or the number of slits may be varied. Engagement means in the form of a snap lock may be provided instead. Furthermore, the top member 321 may be provided with engagement means 327 for engagement with engagement means 328 provided on the inner side of the separator 31. Hereby the separator 31 stays attached to the cover 2 when the cover 2 is removed from the container 1, e.g. for taking out a tissue sample. The engagement means 327, 328 may be in the form of threads or a snap closure.

On top of the top member 321 the membrane 28 is positioned. In FIG. 9 it has a substantially convex shape and in FIG. 10 it has a substantially concave shape. When the pressure is removed from the membrane 28, the membrane 28 will keep its concave shape. This allows personnel to see from above if the preserving agent has been released. As the container 1 is preferably see-through, it may also be seen through the container 1 if the preserving agent has been released. The membrane 28 may be a spring membrane that automatically bounces back to its first position. The puncturing member 323 is activated by pressing the membrane 28. Thereby the puncturing member 323 is displaced along the longitudinal axis of the assembly, and the seal 22, separating the receptacle 211 from the container 1, is ruptured or broken.

In the embodiment shown, the puncturing member 323 is provided with teeth 329 for piercing the seal 22. The puncturing member 323 is made of a polymer material, but may also be made of metal or other suitable materials. An additional piercing element 330 for breaking through the seal 22 is provided, but may be dispensed with.

The seal 22 may be a foil, a film or a polymer membrane.

The separator 31 is adapted to hang from the cover 2. At the bottom 13 of the separator 31 a grid is provided. The separator 31 should be able to let the preserving agent through, and while at the same time ensuring that the seal 22 does not enter the container 1 and securing that the tissue sample 45 does not migrate into the receptacle 211 during transport.

Referring to FIG. 11, the apertures 291 in the grid in the separator 31 are squares, each approx. 1 mm in transverse size, but may be smaller or bigger, circular or polygon-shaped. The grid is permeable for a liquid with a surface tension similar to that of water. Another kind of permeable membrane may also be used. The separator 31 may be provided with apertures elsewhere, such as in the walls of the separator 31. The separator 31 is not a container for the tissue sample such as a cassette, but instead separates the container 1 in two interconnected spaces. The second space 12 and/or the bottom of the container 1 is adapted to receive the tissue sample 45. The first space 11 may also be positioned in the cover 2. Referring to FIGS. 9-11 the separator 31 is furthermore provided with a conduit 30 with an opening or air inlet at the bottom of the separator 31 and an opening or an air outlet positioned at a distance from the air inlet. The air outlet is positioned such that when the seal 22 has been broken and the preserving agent has left the receptacle 211, the preserving agent may not pass the grid due to the smallness of the apertures and the surface tension of the agent, without for example shaking the assembly. The permeability of the grid can be increased by means of the conduit 30 that allows air in the container 1 to bypass the preserving agent through the conduit 30 and thereby letting the preserving agent pass through the apertures 291 in the grid. The opening or air outlet is therefore positioned such that it is above the level of the preserving agent when the seal 22 has been broken. Two conduits 30 are provided in this embodiment, but one of more than two conduits 30 and other shapes of conduits may be provided instead. The separator 31 or at least the grid is blue or another colour of contrast to a tissue sample. This makes it easier to see a tissue sample in case it clings to the separator 31. The separator may be other colours. The space 12 for the tissue sample 45 is positioned below the separator 31. The assembly may be provided with a tracking device such as an RFID (radio frequency identification) tag, such that the sample can be tracked from collection to test in a laboratory. The sample 45 need not be covered by the preserving agent at all times, since the fumes in the container 1 will usually be enough to preserve the sample 45.

FIGS. 12 and 13 show a fourth embodiment of the invention in the form of container assembly 400. FIG. 13 shows a cross section of the assembly along the line A-A as shown in FIG. 12. All the features and functions present in the third embodiment are likewise present in the fourth embodiment where the same reference numbers indicate similar features. The difference between the third and the fourth embodiment is that the fourth embodiment is higher and is able to contain around 20 ml of formalin or other preserving agent both in the receptacle 211 and in the container 1. The conduit(s) 30 has in this embodiment not been made longer as it takes some time before the preserving agent passes the separator 31 and thereby the conduit(s) 30 will still be above the level of the preserving agent when the seal 22 has been broken. The conduit(s) 30 may be made longer, such as between 2-5 cm long. Any size of container able to contain between about 5-50 ml of preserving agent can be imagined.

Figure 14:
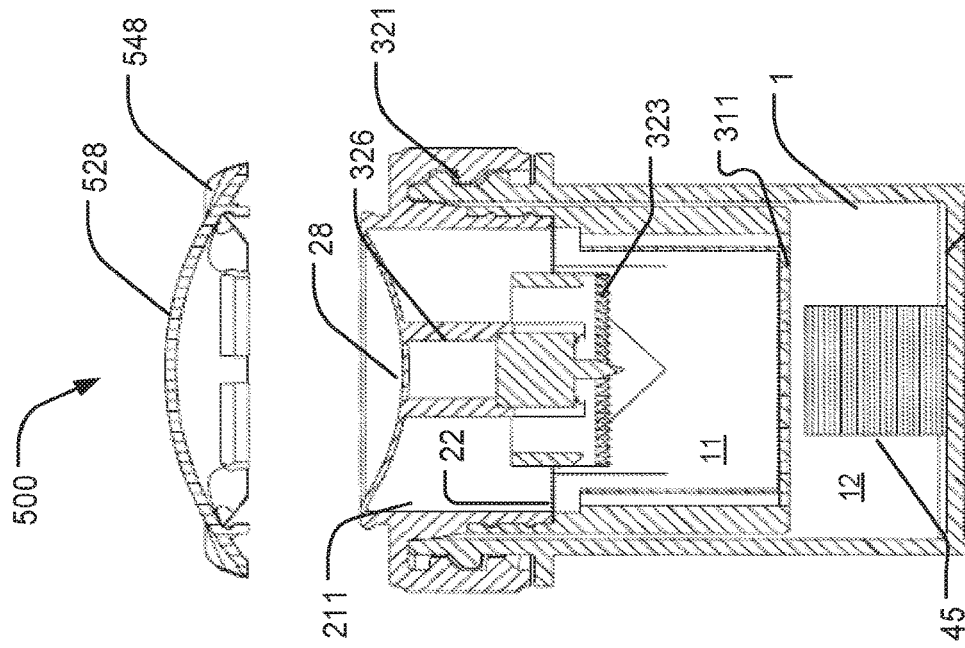
FIG. 14 shows a cross section of the container assembly in a first position in a fifth embodiment.
Figure 15:
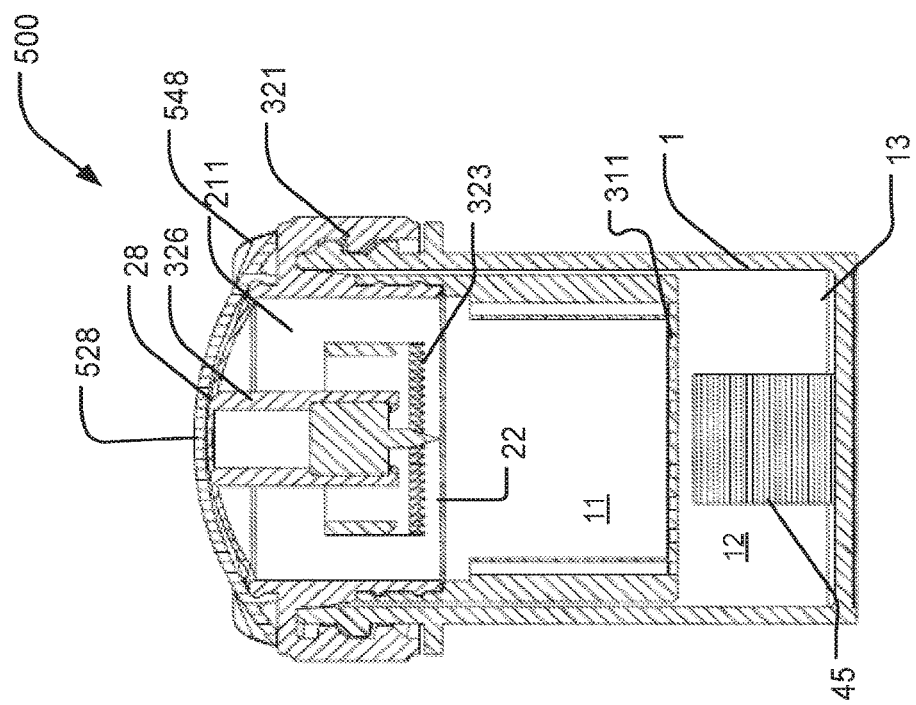
FIG. 15 shows a cross section of the container assembly in a second position in a fifth embodiment.

FIGS. 14 and 15 show a fifth embodiment of the invention in the form of container assembly 500. All the features and functions present in the third and fourth embodiments are likewise present in the fifth embodiment where the same reference numbers indicate similar features. In FIG. 14 the assembly 500 is in a first position and in FIG. 15 the assembly is in a second position. In addition to similar features as those described in the third and/or fourth embodiments, the container assembly 500 further comprises a removable cap 528 provided with gripping parts 548. The cap 528 protects the membrane 28 from pressure during transport.

Figure 16:
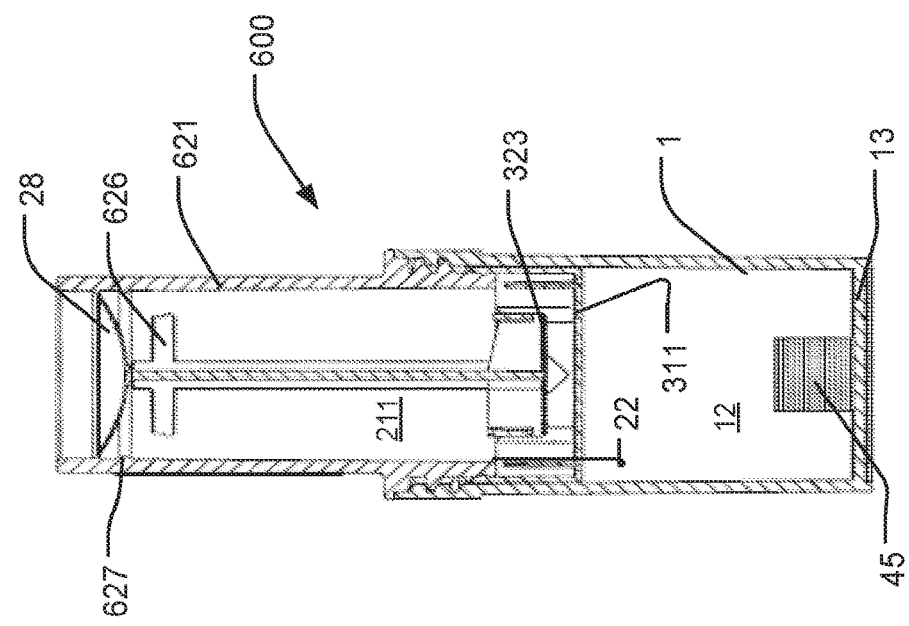
FIG. 16 shows a cross section of the container assembly in a first position in a sixth embodiment.
Figure 17:
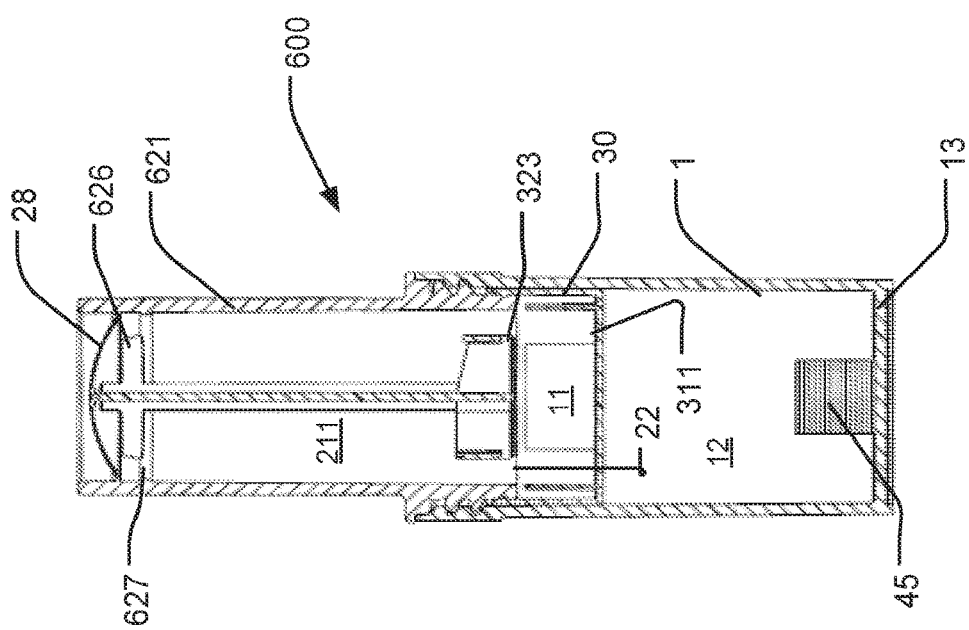
FIG. 17 shows a cross section of the container assembly in a second position in a sixth embodiment.
Figure 18:
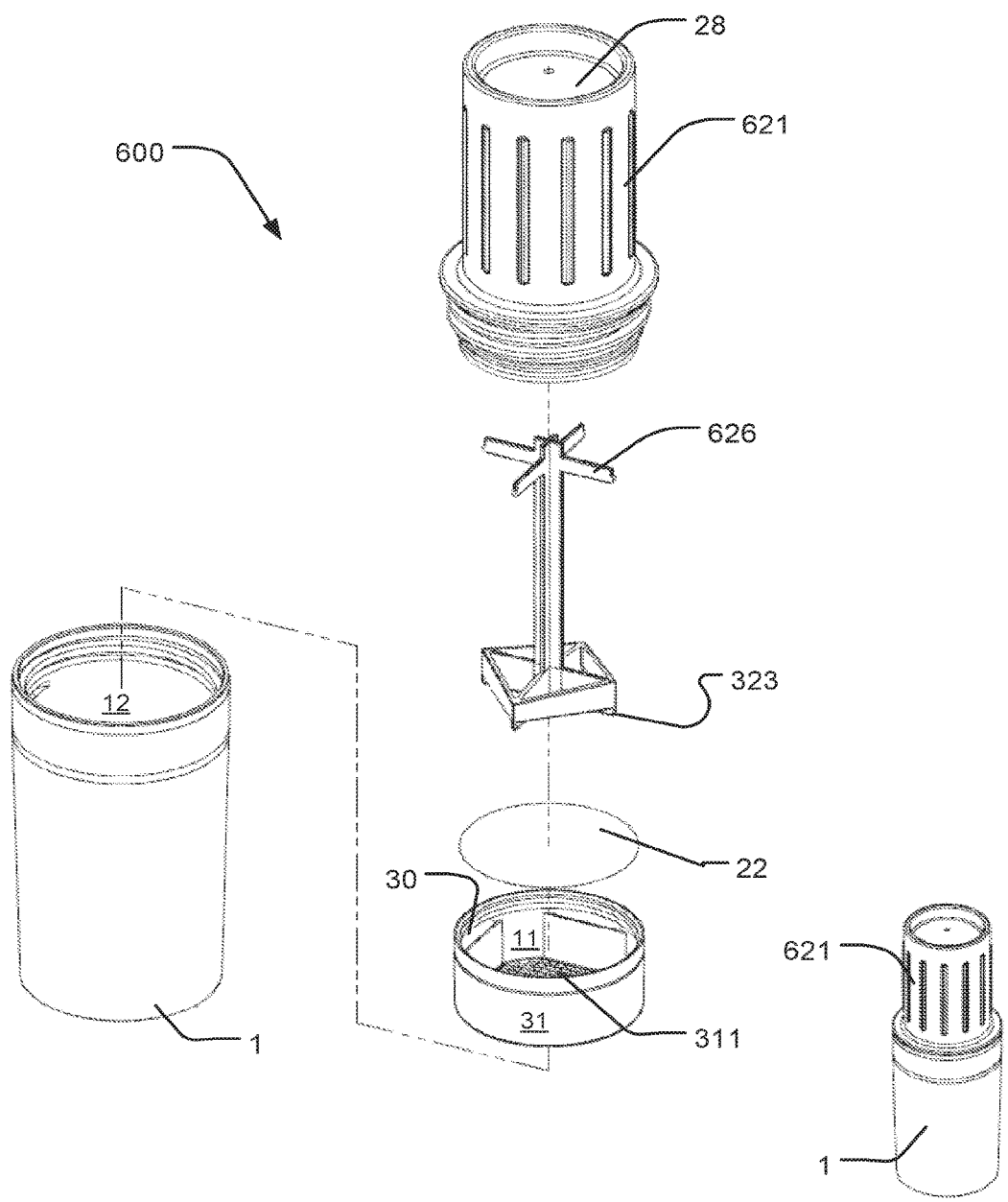
FIG. 18 shows an exploded view the container assembly in a sixth embodiment as well as the container assembly in an assembled state.

FIGS. 16-18 show a sixth embodiment of the invention in the form of container assembly 600. The container assembly 600 differentiates itself among others from the third embodiment in that the top member 621 is taller and is able to contain more preserving agent. The punching or puncturing member 323 is also taller and is provided with a cross shaped or T-shaped projection 626 at the top. The projection 626 rests at a circumferential flange 627 provided on the top member 621. Thereby when the membrane 28 is pushed down, the projection is forced pass the circumferential flange 627 upon which it rested in its initial position. The circumferential flange 627 or the projection 626 may have resilient properties, which allow the projection 626 to pass the circumferential flange 627. The projection 626 may be tapered such that it can be pressed pass the flange 627 more easily. The circumferential flange 627 may also be in the form of circumferential projections that are not connected along the whole circumference. The top member 621 is connectable to the container 1 such that the exterior of the top member 621 engages with the interior of the container 1. It may also be vice versa. The top member 621 and container 1 may be provided with engagement means in form of threads.

Furthermore, the separator 31 is provided with conduit(s) 31 in the form of segments. By extending the wall of the conduit(s) across the separator 31 as a chord, the separator 31 gets more rigid. The conduit(s) 30 do(es) not extend above the top edge of the separator 31, but may do so in other embodiments.

The top member 621 extends above the highest point of the membrane 28 in a first position, thereby protecting the membrane 28 from pressure when no protective cap is provided. The highest point in this embodiment is the center of the membrane.

The sixth embodiment may further comprise any of the features from the third, fourth and fifth embodiment.

Figure 19:
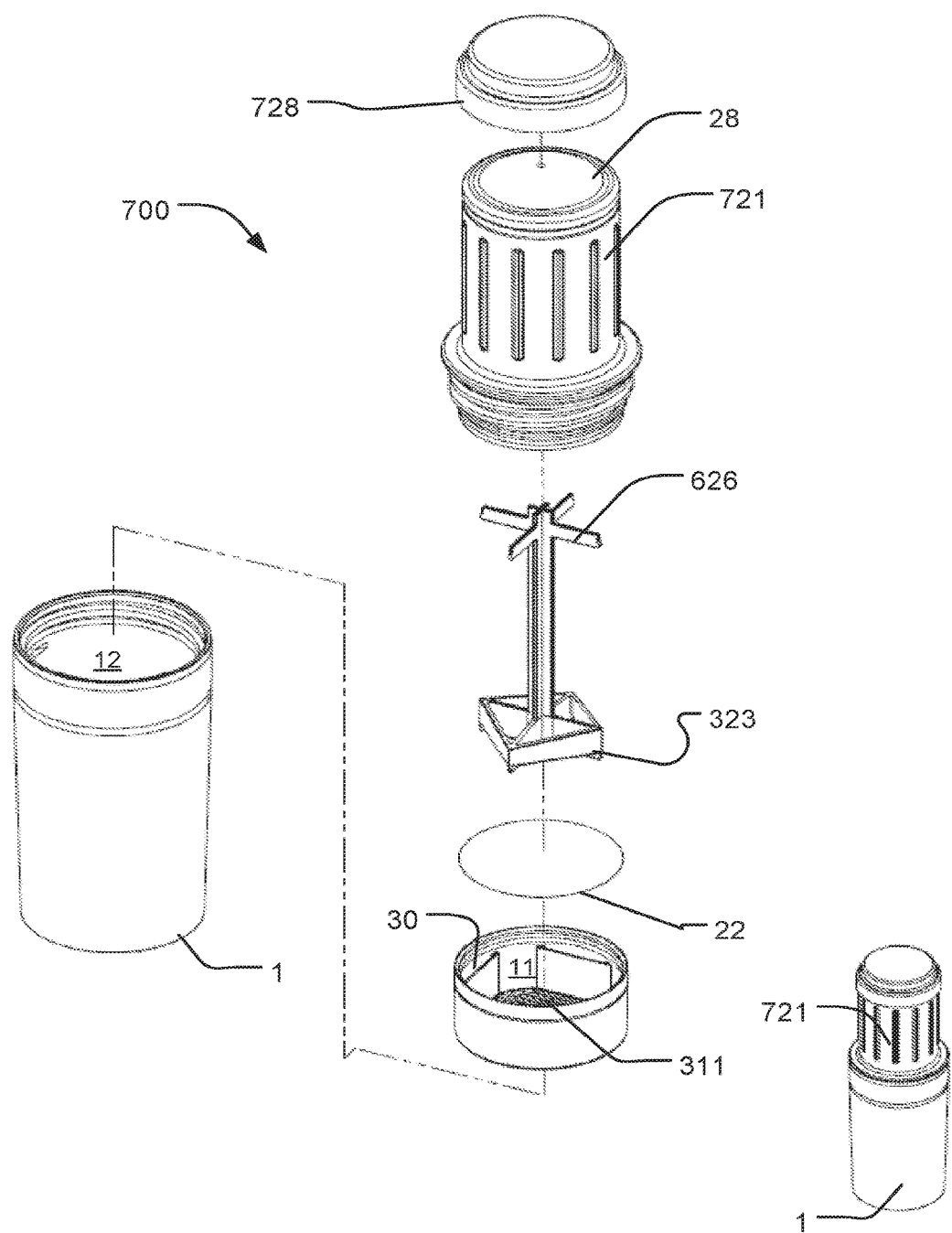
FIG. 19 shows an exploded view the container assembly in a seventh embodiment as well as the container assembly in a perspective view in an assembled state.

FIGS. 19-21 show a seventh embodiment of the invention. In addition to the features in the sixth embodiment the container assembly 700 is additionally provided with a cap 728. The top member 721 does not extend beyond the highest point of the membrane 28 as it does in the sixth embodiment. The seventh embodiment may contain any of the features from the third, fourth, fifth and sixth embodiment.

By "broken" is meant that a hole has been created in the film or seal where either the preserving agent may flow out or particles or contaminants from the outside may enter.

The term "cover" as used herein includes all means that cover the opening of a container. The term "separator" is used for a member used to separate the seal from a potential tissue sample placed in the container. In some embodiments the separator also functions as the punching or puncturing member, such that the separator and the punching member form one element, while in other embodiments the puncturing member and the separator are separate elements.

The word "container" is generally used about the container or space that is adapted to contain the tissue sample.

Furthermore, it is conceivable to make use of other configurations of the container assembly. It may be of industrial size where the container is able to contain at least 1 L or less than 5 L, 10 L, 100 L, 1000 L or more. The container may contain a substance which is to be mixed with a second substance with less of a volume. The cover or lid may be able to contain the second substance, with a volume of less than 5 ml, 10 ml, 30 ml, 50 ml, 100 ml or more than 100 ml, which is to be mixed with the substance in the container. The second substance may be a toxic or volatile substance or a substance where it is important that the exact amount of substance is entered into the container. This larger sized container assembly may have the same features as the first, second, third or fourth embodiment. Any feature of these embodiments may be applied independently of each other to this larger sized container assembly.

In general, the features of the embodiments shown and described may be combined freely and no feature should be seen as essential unless stated in the independent claims.

What is claimed is:

1. A tissue-sample container assembly configured to store a tissue sample, comprising:
    a container defining a cavity for storing the tissue sample; and
    a cover adapted to engage with the container to close the cavity, the cover including a top member having a receptacle containing a preserving agent and a seal for sealing off the receptacle, and including a puncturing member for breaking the seal by displacement of the puncturing member relative to the seal, wherein the puncturing member is adapted to break the seal such that the ruptured seal remains attached to the cover.

2. The container assembly of claim 1, wherein the receptacle and seal cooperate to define an enclosure and a preserving agent is disposed within the enclosure.

3. The container assembly of claim 1, wherein the puncturing member is axially displaceable relative to the seal between at least a first position and a second position, wherein movement of the puncturing member to the second position causes the puncturing member to break the seal placing the receptacle and the container in fluid communication with each other.

4. The container assembly of claim 1, wherein the top member has at least one wall that defines the receptacle and the seal is attached to the at least one wall, wherein the puncturing member is disposed radially inboard of the at least one wall.

5. The container assembly of claim 1, wherein the cover is a lid.

6. The container assembly of claim 1, wherein the cover is adapted to be fluid tightly sealed to the container.

7. The container assembly of claim 1, wherein the container assembly comprises a tracking device.

8. The container assembly of claim 1, wherein the seal is selected from a group consisting of a film, a foil, a membrane, and a polymer.

9. The container assembly of claim 1, wherein the puncturing member is adapted to support the seal after the seal has been broken.

10. The container assembly of claim 1, wherein the puncturing member has at least two projections for breaking the seal.

11. The container assembly of claim 1, wherein the puncturing member has teeth.

12. The container assembly of claim 1, wherein the top member further comprises a membrane defining an outer surface of the top member and having a substantially convex shape in a first position and a substantially concave shape in a second position.

13. The container assembly of claim 12, wherein the cover comprises a protective cap for covering the membrane.

14. The container assembly of claim 1, further comprising an indicator for indicating whether the seal has been broken.

15. A method of preserving a tissue sample comprising:
    providing a container;
    providing a cover including a puncturing member and a top member with a receptacle filled with a preserving agent and sealed with a seal;
    placing a tissue sample in said container;
    engaging said cover with the container; and
    displacing the puncturing member to rupture the seal and release the preserving agent into the container.

16. A tissue-sample container assembly comprising:
    a container defining a cavity configured to store a tissue sample;
    a lid connectable to the container to close the cavity, the lid including:
        a receptacle adapted to contain a preserving agent,
        a seal forming at least a portion of a bottom of the receptacle, and
        a puncturing member arranged above the seal and actuatable to break the seal; and
    a preserving agent disposed in the receptacle.

17. The container assembly of claim 16, wherein the puncturing member is disposed in the receptacle.

18. The container assembly of claim 17, wherein the lid further includes a compressible top and the puncturing member is suspended from the top, and wherein the puncturing member is actuated through the seal to release the preserving agent onto the tissue sample by compressing the top.

19. The container assembly of claim 16, wherein the puncturing member functions as a separator.

20. The container assembly of claim 16, wherein the puncturing member functions as a separator at least after the seal has been broken.

* * * * *